(12) United States Patent
Diehl

(10) Patent No.: US 7,761,132 B2
(45) Date of Patent: Jul. 20, 2010

(54) LOCAL ENDO COIL FOR INTRACORPOREAL PLACEMENT FOR RECORDING MAGNETIC RESONANCE SIGNALS

(75) Inventor: Dirk Diehl, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 899 days.

(21) Appl. No.: 11/324,225

(22) Filed: Jan. 4, 2006

(65) Prior Publication Data

US 2006/0184009 A1 Aug. 17, 2006

(30) Foreign Application Priority Data

Jan. 4, 2005 (DE) ........................ 10 2005 000 761

(51) Int. Cl.
*A61B 5/05* (2006.01)
*A61M 29/00* (2006.01)
*A61M 31/00* (2006.01)

(52) U.S. Cl. ................. 600/423; 600/420; 600/421; 600/422; 606/192; 604/103.14

(58) Field of Classification Search ............... 600/410, 600/421–423
See application file for complete search history.

(56) References Cited

U.S. PATENT DOCUMENTS

| | | | |
|---|---|---|---|
| 5,413,104 A | 5/1995 | Buijs et al. | |
| 5,451,232 A | 9/1995 | Rhinehart et al. | |
| 5,476,095 A * | 12/1995 | Schnall et al. | 600/423 |
| 6,437,569 B1 * | 8/2002 | Minkoff et al. | 324/318 |
| 6,746,465 B2 * | 6/2004 | Diederich et al. | 606/192 |
| 2002/0161421 A1 * | 10/2002 | Lee et al. | 607/116 |
| 2003/0028095 A1 * | 2/2003 | Tulley et al. | 600/422 |
| 2003/0055449 A1 * | 3/2003 | Lee et al. | 606/194 |
| 2004/0024434 A1 * | 2/2004 | Yang et al. | 607/96 |
| 2004/0119474 A1 | 6/2004 | Skloss | |
| 2005/0165301 A1 * | 7/2005 | Smith et al. | 600/421 |

FOREIGN PATENT DOCUMENTS

| | | |
|---|---|---|
| DE | 42 33 809 A1 | 5/1993 |
| DE | 693 16 838 T2 | 5/1994 |
| DE | 101 42 394 A1 | 11/2002 |
| DE | 103 57 604 A1 | 7/2004 |

OTHER PUBLICATIONS

Qiu, B., Yeung, CJ., Du, X., Atalar, E., and Yang, X. "Development of an Intravascular Heating Source Using an MR Imaging Guidewire." Journal of Magnetic Resonance Imaging. vol. 16, pp. 716-720, Mar. 2002.*

* cited by examiner

*Primary Examiner*—Long V Le
*Assistant Examiner*—Angela M Hoffa
(74) *Attorney, Agent, or Firm*—Staas & Halsey LLP

(57) ABSTRACT

An outer balloon is provided in the interior thereof with a coil conductor for a local endo coil for intracorporeal placement for recording magnetic resonance signals, which can be deployed for the purpose of receiving signals. In addition to the coil, a filling medium is fed into the balloon, so that the deployed coil conductor is surrounded at least in sections by at least one material having a dielectric constant $\epsilon_r > 1$.

23 Claims, 2 Drawing Sheets

LOCAL ENDO COIL FOR INTRACORPOREAL PLACEMENT FOR RECORDING MAGNETIC RESONANCE SIGNALS

CROSS REFERENCE TO RELATED APPLICATIONS

This application is based on and hereby claims priority to Application No. 10 2005 000 761.9 filed on Jan. 4, 2005, the contents of which are hereby incorporated by reference.

BACKGROUND OF THE INVENTION

1. Field of the Invention

The invention relates to a local endo coil for intracorporeal placement for recording magnetic resonance signals, having an outer balloon and, provided in the interior thereof, a coil conductor, which two can be deployed for the purpose of receiving signals by means of feeding a filling medium.

2. Description of the Related Art

Local coils are frequently used in imaging by magnetic resonance tomography for the purpose of locally raising the sensitivity during reception of the magnetic resonance signal. The raised sensitivity leads to a higher signal-to-noise ratio and thus to improved imaging in the surroundings of the local coil. Local coils that are inserted into body openings, for example, the rectum, are sometimes used for recording images from the body interior. With these local endo coils, the metallic structure, that is to say the actual coil loop, that picks up the signals is surrounded by an elastic balloon. The balloon and, possibly, a further inflatable plastic structure on which the coil loop is suspended and which is arranged inside the balloon, are filled from outside with air via feeders. The air-filled outer balloon produces the space required in the body interior to deploy the coil loop, for example by means of the further inflatable plastic structure. The deployed coil loop can bear directly against the inner wall of the balloon over long sections, and is then separated from the patient's tissue only by the slight wall thickness of the balloon. In certain circumstances, for example given maloperation or cable rupture or the like, elevated high-frequency currents can occur on the coil loop and/or electric supply lead thereof which are driven by the transmitting body coil of the magnetic resonance tomograph, and, as displacement currents, enter the adjacent tissue, where a high increase in local specific absorption rate (SAR) occurs. The high current density, which comes about precisely wherever the coil loop lies closest to the tissue, that is to say wherever the capacitance is greatest, leads to an impermissibly high thermal loading of the tissue, as far as that of local burns.

Sheath wave traps can be used to prevent the high sheath currents on the coil loop or supply lead thereof. However, for reasons of cost these are not used with the local endo coils, which are intended as a rule to be used once.

SUMMARY OF THE INVENTION

The invention is therefore based on the problem of specifying a local endo coil that provides a remedy here and which prevents an impermissibly high local tissue loading during imaging, that is to say when the local endo coil is placed and ready for operation.

To solve this problem, it is provided, according to an aspect of the invention in the case of a local endo coil of the type mentioned at the beginning that apart from the balloon, the deployed coil conductor is surrounded at least in sections by at least one material having a dielectric constant>1.

Otherwise than with known local endo coils, thus, the metal coil conductor is operating, that is to say, deployed, and MR images can be recorded, it is surrounded not by air as inflatable medium of use, but also, in addition to the balloon which would be much too thin, by a material that has a dielectric constant>1, the aim being for the dielectric constant to be as high as possible, preferably >10 or even >50. That is to say, to reduce the current concentration in the adjacent tissue, the (dielectric) conductivity is raised in the immediate vicinity of the coil conductor, as a result of which the current flowing into the tissue is distributed over a substantially larger cross section. Even when the coil conductor bears directly against the balloon wall, the "conductive" conductor surroundings provided according to the invention have the effect that the current flows off over a large area, and is not concentrated on to the immediate vicinity in the region immediately bearing on to the tissue. As before, it is true that at the MR frequency, which can build up between the conductor loop and the patient and/or the tissue, the AC voltage drives a (dielectric or displacement) current through the electrically nonconductive interspace between the coil conductor and tissue, that is to say with the balloon material bearing directly, the highest current density in relation to the adjacent tissue coming about where the intermediate layer is thinnest (that is to say the capacitance is greatest). However, there is nevertheless a substantial improvement with regard to the conductivity of the immediate conductor surroundings, the effect of which is that a substantial amount of current can flow off thereby into the tissue, and that consequently not all the amount of current flows off in the region where the capacitance is greatest and the intermediate layer is thinnest. As a consequence of the distribution of current over a larger area, the local SAR load is substantially reduced in comparison with the previously known coils, and so no impermissibly high patient burden occurs.

It is provided in a first, simple configuration of the invention that the material having the high dielectric constant and surrounding the coil conductor when ready for operation or recording is the filling medium led into the balloon via a feeder. That is to say, the balloon and the feeder etc. are designed to hold an appropriate filling medium, it being possible to use a liquid or a gel as filling medium. It is particularly expedient for water, whose dielectric constant is approximately 80 (at 20° C.), to be used for this purpose. The use of water as filling medium that surrounds the coil conductor, which is preferably spaced apart somewhat from the inner wall of the outer balloon in the deployed state, is advantageous to the effect that there is thereby a matching of the dielectric constant ($\in_r$ value) of the filling medium and that of the surrounding patient tissues which does, overall, primarily likewise consist of or contain, water, the result of this being a more uniform flow of current in all directions. Consequently, there is a substantial reduction in current density by comparison with the previously known air filling.

Given a local coil configuration in which the coil conductor is arranged on a structure that can be deployed by a further one that can be filled with a further filling medium which can be supplied via a feeder, one development of this idea of the invention, specifically to accomplish the raising of the dielectric constant via the filling medium, provides here, as well, to use as filling medium, a liquid or a gel having a dielectric constant>1 to fill this inner structure such that the filling medium having a high dielectric constant is therefore also present in this region, given a deployed coil conductor. This is advantageous to the effect that the result is now also a current flow directed inward, that is to say toward the balloon interior, and which flows off via the inner part. Moreover, the electric conductivity of the filling medium also has the effect that the irradiated power is already partially converted in the filling medium itself, and is therefore not output into the surrounding tissue. The filling medium, that is to say the water, for example, reduces the thermal loading of the surrounding tissue by the heat transport, which is increased by comparison with the air filling, be this owing to the thermal conduction or the natural and/or forced convection, and ensures a heat dissipation inward and a more uniform temperature distribution, and thus a reduction of so-called hot spots.

To raise yet further the dielectric constant of the filling medium, for example, of the water, it is expedient when the liquid used or the gel used is mixed with solid particles, for example with ceramic particles that have a very high $\in_r$. Mention may be made by way of example of $CaTiO_3$ having an $\in_r=150\text{-}165$, $(SrBi)TiO_3$ having an $\in_r=900\text{-}1000$ or $(BaTiO_3)_{0.9}*(BaZrO_3)_{0.075}$ having an $\in_r=2700\text{-}3000$, this enumeration not being exhaustive. It is also possible to use other titanium oxides or titanates, it being possible in principle to use all the known capacitor ceramics. These are added in the form of fine particles.

With regard to the fact that water inherently has a somewhat disturbing effect on MR imaging since it somewhat worsens the contrast owing to its high relaxation time, one advantageous development of the invention provides that the liquid or the gel is mixed with at least one substance shortening the relaxation time, for which customary MR contrast media such as, for example, Gd-DTPA or $MnCl_2$ can be used.

As described, the use, for example of a water filling both of the outer balloon and of the inner structure already effects a substantial reduction in current density by comparison with the prior air filling. However, the highest current density continues to occur in the immediately adjoining tissue, but without leading to the impermissibly high burdens. Nevertheless, a further reduction in current density is desirable, and this can be accomplished according to the invention by providing a partial sheathing of the coil conductor that is directed toward the balloon and has a dielectric constant that is lower than that of the filling medium. The dielectric conductivity in the space between the conductor loop and the tissue is reduced via this partial sheathing, and so the dielectric or displacement current preferably flows off into the tissue around this partial sheathing and via the water. The partial sheathing encloses the conductor loop, preferably only with a half side on the side facing the tissue.

Alternatively, or in addition to using an appropriately suitable filling medium, according to one further alternative embodiment of the invention, it is possible to provide the coil conductor generally with a sheathing made from at least one material having a dielectric constant $\in_r>1$ preferably $>10$ or even $>50$, that is to say to lay a dielectric sheath around the coil conductor. Owing to the locally raised conductivity effected via the dielectric sheath, this design effects a substantial reduction in current density even when air is used as filling medium. As also in the case of the use of water, for example as filling medium, it is expedient here for the purpose of varying the conductivity when the sheathing has a lower dielectric constant in the region directed toward the outer balloon than in the region bordering on the balloon interior or this region with direct bearing. That is to say via an appropriate configuration of the sheathing in the region of the immediate, shortest transition to the tissue, the conductivity is likewise worsened, by comparison with the remaining conductivity of the dielectric sheathing. For example, it may be conceived to provide a two-component sheathing having a first partial sheathing approximately surrounding the coil conductor completely and into which or onto which there is inserted or applied a second sheathing which bears directly against the balloon inner wall and has a lower dielectric constant. This sheathing is generally dielectrically conductive, but its conductivity differs locally in such a way that it is low directly toward the outside of the balloon.

According to the invention, then, a locally varying and/or anisotropic dielectric conductivity—referred to the sheathing cross section—should be provided, that is to say a lower conductivity toward the balloon and a higher conductivity in some regions the more the current is directed toward the balloon interior. By way of example, ceramics whose $\in_r$ values are a function of direction can be used as sheathing material having a corresponding anisotropic dielectric conductivity. If, instead of anisotropic materials, use is made of isotropic ones, these can be applied in the form of layers to implement spatially different, direction-dependent conductivities for which purpose layers are applied that are composed of a material having a high conductivity, and a material having a low conductivity, or having a correspondingly low $\in_r$ value and high $\in_r$ value. A useful difference in conductivity can thereby be achieved. As a result of this, a small resulting $\in_r$ value can come about perpendicular to the layer planes (corresponding to a series connection of capacitances), while high $\in_r$ values (corresponding to a parallel connection) result for directions lying in the respective layer plane.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
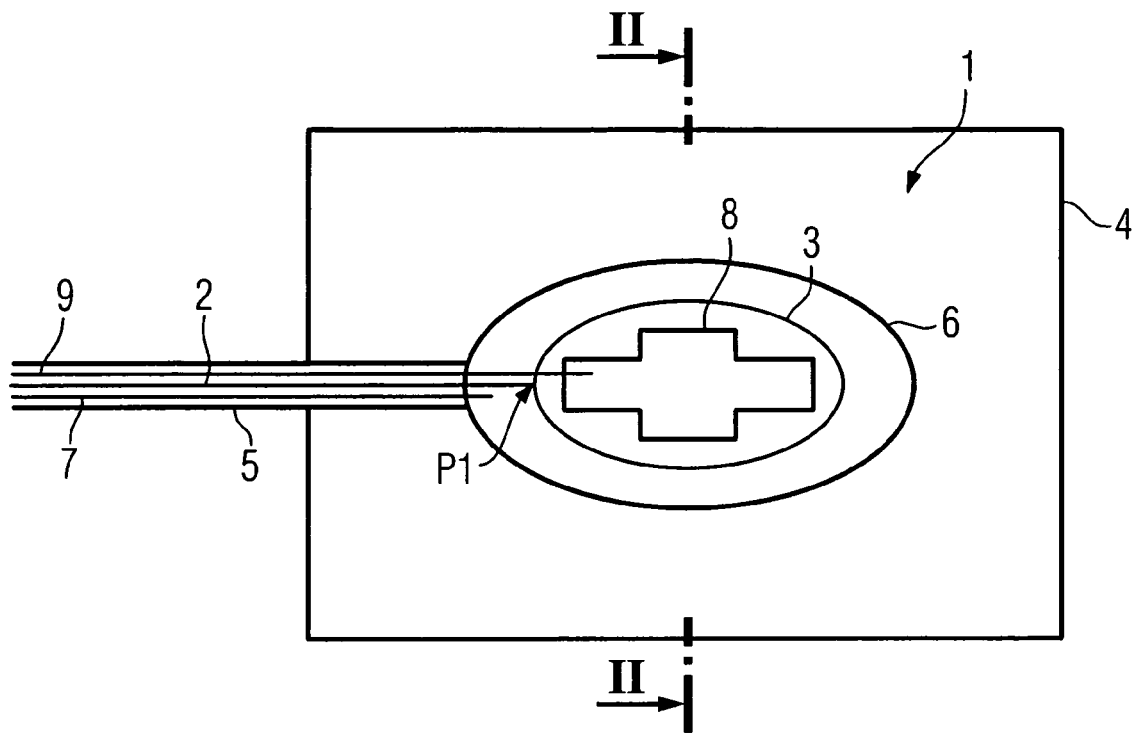
FIG. 1 is a schematic of a local endo coil according to the invention in the deployed state in the form of a plan view of the annularly opened coil conductor.

Reference will now be made in detail to the preferred embodiments of the present invention, examples of which are illustrated in the accompanying drawings, wherein like reference numerals refer to like elements throughout.

FIG. 1 shows a schematic of a local endo coil 1 according to the invention with a coaxial supply lead 2 whose outer conductor (sheath) ends at the point P1. The inner conductor, which is continued, forms the conductor loop 3 whose end makes contact again at the end of the outer conductor at the point P1. The conductor loop 3 and a part of the coaxial supply lead 2 are inserted into a body opening of the patient, for example, the rectum. The conductor loop 3 then serves for acquiring the largely undamped MR signal inside the patient.

The coaxial supply lead 2 itself is covered by an insulation 5 that prevents the metallic outer conductor from being in direct electric contact with the patient.

To provide in the interior of the patient a space for the deployment of the conductor loop 3, which is folded together during the insertion so that the entire instrument body is as narrow as possible and can be inserted, and likewise to prevent direct electric contact between the conductor loop 3 and the surrounding tissue, a balloon 6 made from flexible plastics or rubber material and which completely surrounds the conductor loop is provided and is arranged on the insulation 5. After the insertion, the balloon 6 is filled from outside with a filling medium—previously air—thus previously inflated, via a hose 7 guided in a fashion parallel to the coaxial supply lead 2. In this embodiment, the conductor loop 3 is deployed via a further flexible structure 8 formed of plastic or rubber that is led past a further supply lead 9, which is likewise led inside the insulation 5 and on which the conductor loop 3 is fastened. This structure 8, which is designed in the fashion of a cushion is also inflated with air in the related art.

Figure 2:
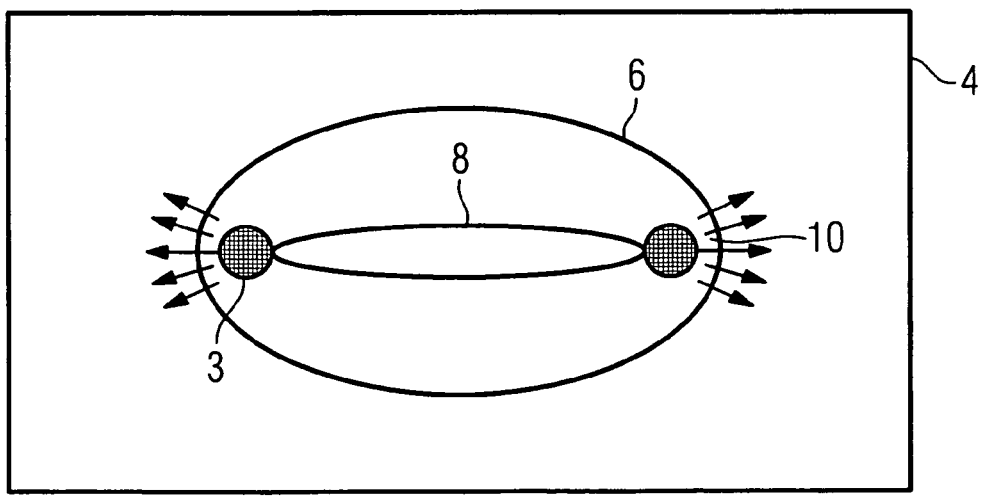
FIG. 2 is a sectional view through the balloon body from FIG. 1 along the lines II-II for the purpose of illustrating the impermissibly high current densities resulting in the related art.

FIG. 2 shows a section through the deployed structure along the lines II-II in FIG. 1. It shows the inflated outer balloon 6, the inner inflated structure 8 and the coil conductor 3, which may be seen to be fastened on the structure 8. The AC voltage at the MR frequency that can be built up between the coil conductor 3 and the patient 4 drives a dielectric or displacement current through the electrically nonconductive interspace 10 between the coil conductor 3 and the tissue. Specifically, in the deployed state the coil conductor sometimes bears at the edge against the balloon inner wall such that the interspace is formed exclusively by the thin wall thickness of the balloon 6. The capacitance is greatest in this interspace, where the intermediate layer or the width of the space is narrowest, and so the highest current density and thus also the highest HF losses come about in the adjacent tissue, and a locally excessively increased SAR burden can occur together with possible tissue damage from burns.

To reduce the local HF losses in the tissue, it is necessary to reduce the current concentration in the adjacent tissue. According to the invention, the (dielectric) conductivity in the immediate surroundings of the conductor loop is raised by comparison with the air filling described in FIGS. 1 and 2, the result being that the current into the tissue is distributed over a larger cross section.

Figure 3:
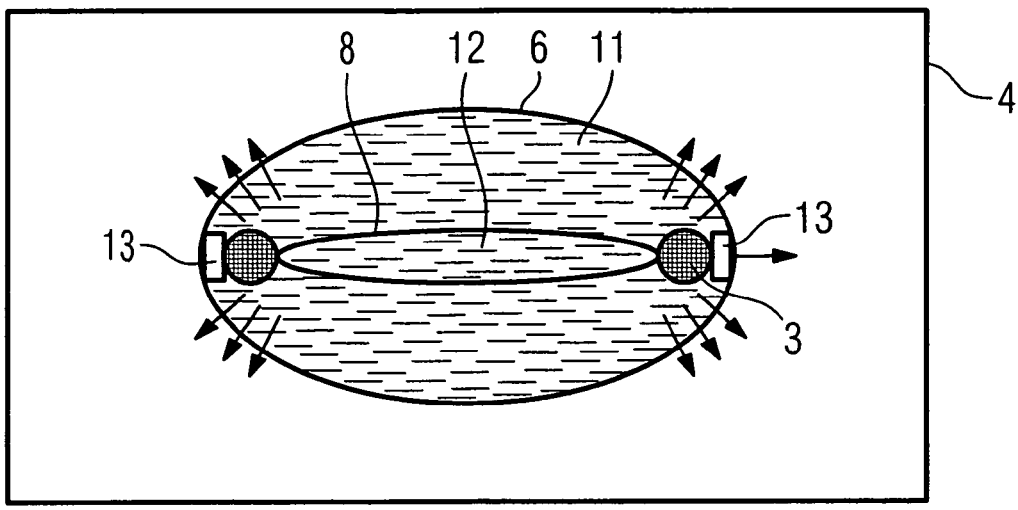
FIG. 3 is a schematic of an embodiment of the local endo coil according to the invention having a liquid or gel filling.

FIG. 3 here shows the simplest form of an improvement, specifically that the balloon 6, as also here the inflatable structure 8, is filled with a filling medium 11 or 12 in the form of a liquid, in particular water having a dielectric constant of $\in_r=80$. The balloon and the structure are thus designed in such a way and/or composed of a material such that they can be filled with a liquid, here water, at a satisfactory pressure. They are preferably composed of a sufficiently stable plastic, for example, PET or the like. By comparison with the non-conductive interspace as shown in FIG. 2, the water filling results in a substantially higher conductivity in the conductor surroundings, and so it is ensured that the dielectric or displacement current flows off into the tissue over a large area and no longer with a locally high current density. Also associated with the use of water as filling medium is a matching of the $\in_r$ values to the surrounding tissue, this resulting in a more uniform flow of current in all directions. The advantage of the use of water results, furthermore, in a reduction in the thermal loading of the surrounding tissue, into which current continues to flow, and a more uniform temperature distribution comes about owing to the greatly increased heat transport by comparison with the air filling.

In the embodiment shown in FIG. 3 there is provided for the purpose of further improvement a partial sheathing 13 of the coil conductor that is illustrated here, by way of example in the form of the rectangle, but which partially surrounds the coil conductor and is arranged permanently thereon. The partial sheathing 13 is arranged on the coil conductor 3 such that it spaces the latter from the inner wall of the balloon 6. The sheathing 13 is composed of a material that has a lower dielectric conductivity or dielectric constant than the filling medium 11 or 12, that is to say water, here. Thus, as a result the conductivity between the coil conductor and tissue is lower over the shortest distance than illustrated in FIG. 3 toward the side that is to say the current, also illustrated here by the arrows, preferably flows off into the tissue via the water filling, and therefore over a yet larger area. Any material may be used as sheathing material, for example, ceramics or the like, but of course appropriate plastics, etc. are also suitable. It is further to be pointed out at this juncture that the respective filling medium 11, 12 can be mixed, for example with ceramic particles or the like that serve to raise the entire $\in_r$ value of the filling medium. Again, substances that shorten relaxation time, for example suitable MR contrast media that have this property can also be added to the respective filling media 11 or 12 to avoid the image impairment resulting from a long relaxation time, which water usually has.

Figure 4:
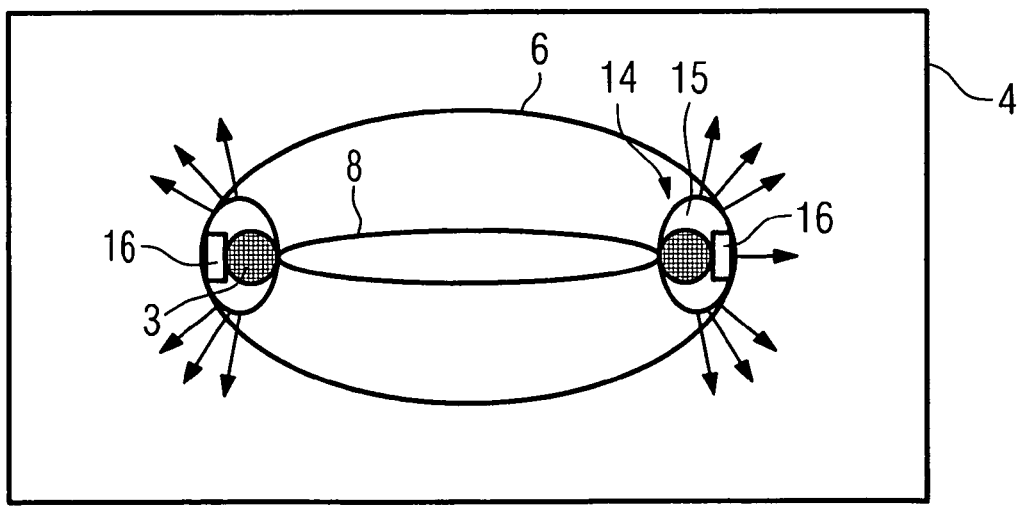
FIG. 4 is a schematic of an embodiment of a local endo coil according to the invention having a dielectric sheathing.

A further inventive embodiment of a coil conductor is shown in FIG. 4. The basic design of the coil conductor is the same as described with reference to the embodiments above. Here, as well, an outer balloon 6, an inflatable inner structure 8 and the deployable coil conductor 3 arranged on the structure are provided. In this embodiment, as illustrated, the balloon 6 and the structure 8 are inflated with air, as known in the related art. To implement a substantial lowering of the current concentration in the immediately adjacent tissue, the coil conductor 3 is provided with a sheathing 14 that has two sheath parts 15 and 16 in the exemplary embodiment shown. The sheath part 15, which approximately completely surrounds the coil conductor is composed of a material having as high a dielectric constant as possible, for example one of the ceramics mentioned at the beginning, which can be applied with suitable carrier materials that form a matrix. The second sheath part 16 is in turn formed of a material having a lower dielectric constant by comparison with the sheath part 15 in order here also to implement in turn a locally varying electric conductivity, that is to say the conductivity directly into the tissue, therefore by the shortest way, is poor, while the conductivity in correspondingly far removed tissue regions is substantially better. Of course, in the case of the use of a sheathed coil conductor it is also possible to use a balloon or a structure that is designed for holding water, for example, since the water filling is advantageous both electrically and thermally.

As an alternative to the use of a quasi two-component sheathing 14 it is also conceivable to use a sheath having an anisotropic dielectric conductivity and that in the arrangement shown in FIG. 4 has a lower $\in_r$ value in the horizontal direction, and a high $\in_r$ value in the vertical direction, for which greater distance between the coil conductor 3 and tissue is present here. It is possible, in turn, also to make use of ceramics for this purpose with $\in_r$ values that are a function of direction, although in this case, as well, a multicomponent structure implemented via appropriate material layerings is suggested.

Overall, the inventive local endo coil designed for holding liquid or having the sheathing permits the HF currents to flow off over a substantially larger area into the surrounding tissue owing to the high dielectric conductivity of the selected filling medium or else to the sheathing used. High local power loss densities, such as occur given air filling in the immediate surroundings of the coil loop without use of the measures according to the invention are avoided. The electric conductivity of the filling medium such as water, for example has the effect that the irradiated power is partially already converted in the medium, and that therefore the surrounding tissue is detectably relieved.

Given the use of a sheathing with a material combination having a high and low relative dielectric constant, it is possible to lead the displacement or HF currents in such a way that the current density and thus the SAR loading are reduced in the otherwise highly loaded tissue in the immediate surroundings of the coil loop or the supply lead.

Of course, it is also conceivable to use a liquid or gel-type conductive filling medium and a sheathing.

Overall, the inventive local endo coil advantageously permits a reduction of the total power loss that is converted in the tissue, on the basis of the reduced contact resistance when a constant total current that flows off into the tissue from the coil structure is assumed.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV,* 69 USPQ2d 1865 (Fed. Cir. 2004).

What is claimed is:

1. A local endo coil for intracorporeal placement, for recording magnetic resonance signals, which can be deployed and unfolded for the purpose of receiving signals, comprising:
    an outer balloon having an interior and a first feeder;
    a coil conductor in the interior of said outer balloon;
    at least one liquid or gel filling the interior of the outer balloon via the first feeder, including an area between the coil conductor and the outer balloon, the at least one liquid or gel having a first dielectric constant greater than one in order to reduce the thermal loading of tissue in an area of the local endo coil; and
    a deployable structure disposed inside the outer balloon and having a second feeder, the deployable structure supporting the coil conductor on an outer surface thereof and being filled via the second feeder with a medium different from the at least one liquid or gel, the medium having a second dielectric constant greater than the first dielectric constant.

2. The local endo coil as claimed in claim 1, wherein the at least one liquid or gel is water.

3. The local endo coil as claimed in claim 1, wherein the at least one liquid or gel is also mixed with at least one substance shortening a relaxation time of the at least liquid or gel.

4. The local endo coil as claimed in claim 1, wherein the medium is a liquid or a gel.

5. The local endo coil as claimed in claim 4, wherein the medium is water.

6. The local endo coil as claimed in claim 5, wherein the medium is mixed with solid particles.

7. The local endo coil as claimed in claim 5, wherein the medium is mixed with at least one substance shortening a relaxation time of the medium.

8. The local endo coil as claimed in claim 4, wherein the medium is mixed with solid particles.

9. The local endo coil as claimed in claim 4, wherein the medium is mixed with at least one substance shortening a relaxation time of the medium.

10. The local endo coil as claimed in claim 4, wherein said coil conductor has an at least partial sheathing with a third dielectric constant lower than the first and second dielectric constants.

11. The local endo coil as claimed in claim 10, wherein the at least partial sheathing of said coil conductor is made from at least one material having a dielectric constant greater than one.

12. The local endo coil as claimed in claim 11, wherein the at least partial sheathing has a lower dielectric constant in a first region directed toward an exterior of said outer balloon than in a second region directed toward a center of said outer balloon.

13. The local endo coil as claimed in claim 12, wherein the at least partial sheathing is formed of a first material surrounding the coil conductor on the first region directed toward an exterior of said outer balloon and of a second material enclosing remaining portions of said coil conductor.

14. The local endo coil as claimed in claim 13, wherein the at least partial sheathing is dielectrically conductive.

15. The local endo coil as claimed in claim 14, wherein the at least partial sheathing has a dielectric conductivity that is at least one of locally varying and anisotropic.

16. The local endo coil as claimed in claim 1, wherein the at least one liquid or gel is mixed with solid particles.

17. A method of deploying a local endo coil, formed of an outer balloon, having an interior and a first feeder, and a coil conductor therein, at least one liquid or gel filling the interior of the outer balloon via the first feeder, and a deployable structure disposed inside the outer balloon and having a second feeder, the deployable structure supporting the coil conductor on an outer surface thereof, for intracorporeal placement for recording magnetic resonance signals for the purpose of receiving signals, comprising:
    folding the outer balloon and coil conductor therein and inserting the folded outer balloon and coil conductor;
    after inserting the folded outer balloon and coil conductor, unfolding the outer balloon and coil conductor by feeding the at least one liquid or gel into the outer balloon via the first feeder to fill an interior of the outer balloon, including an area between the coil conductor and the outer balloon, the at least one liquid or gel having a dielectric constant greater than one in order to reduce the thermal loading of tissue in an area of the local endo coil; and
    filling the deployable structure with a medium different from the at least one liquid or gel via a second feeder.

18. A local endo coil for intracorporeal placement, for recording magnetic resonance signals, which can be deployed and unfolded for the purpose of receiving signals, comprising:
    an outer balloon having an interior and a first feeder;
    a coil conductor in the interior of said outer balloon;
    at least one liquid or gel filling the interior of the outer balloon via the first feeder, including an area between the coil conductor and the outer balloon, the at least one material having a first dielectric constant greater than one in order to reduce the thermal loading of tissue in an area of the local endo coil; and
    a deployable structure disposed inside the outer balloon and having a second feeder, the deployable structure supporting the coil conductor on an outer surface thereof and being filled via the second feeder with a medium different from the at least one liquid or gel, the medium having a second dielectric constant greater than the first dielectric constant, wherein said coil conductor has an at least partial sheathing with a lower dielectric constant in a first region directed toward an exterior of said outer balloon than in a second region directed toward a center of said outer balloon.

19. The local endo coil as claimed in claim 18, wherein the at least one material is a filling medium led into said outer balloon via a feeder.

20. The local endo coil as claimed in claim 19, wherein the filling medium is a liquid or a gel.

21. The local endo coil as claimed in claim 20, wherein the liquid or the gel is mixed with solid particles.

22. The local endo coil as claimed in claim 18, wherein the at least partial sheathing has a second dielectric constant lower than the first dielectric constant.

23. The local endo coil as claimed in claim 18, wherein the at least partial sheathing is formed of a first material surrounding the coil conductor on the first region directed toward an exterior of said outer balloon and of a second material enclosing remaining portions of said coil conductor.

* * * * *